United States Patent
Northcott et al.

(10) Patent No.: US 8,132,912 B1
(45) Date of Patent: Mar. 13, 2012

(54) IRIS IMAGING SYSTEM USING CIRCULAR DEFORMABLE MIRROR MOUNTED BY ITS CIRCUMFERENCE

(75) Inventors: Malcolm J. Northcott, Felton, CA (US); J. Elon Graves, Los Gatos, CA (US); Dan Potter, Campbell, CA (US); Siegfried Fleischer, Campbell, CA (US)

(73) Assignee: AOptix Technologies, Inc., Campbell, CA (US)

( * ) Notice: Subject to any disclaimer, the term of this patent is extended or adjusted under 35 U.S.C. 154(b) by 239 days.

(21) Appl. No.: 12/494,087

(22) Filed: Jun. 29, 2009

Related U.S. Application Data

(60) Provisional application No. 61/076,644, filed on Jun. 29, 2008.

(51) Int. Cl.
*A61B 3/14* (2006.01)
*G02B 26/08* (2006.01)
*G02B 26/10* (2006.01)
*G02B 26/12* (2006.01)

(52) U.S. Cl. ............... 351/206; 351/209; 359/224.1

(58) Field of Classification Search .......... 351/206, 351/208–210, 220, 221; 359/221.2–221.4, 359/223.1–226.2, 234, 871–881
See application file for complete search history.

(56) References Cited

U.S. PATENT DOCUMENTS

| | | | |
|---|---|---|---|
| 6,328,451 B1 * | 12/2001 | Lang ........................ | 359/871 |
| 6,464,364 B2 * | 10/2002 | Graves et al. ............. | 359/846 |
| 6,568,647 B2 * | 5/2003 | Graves et al. ............. | 248/476 |
| 7,269,344 B2 * | 9/2007 | Nishioka et al. .......... | 396/60 |
| 2003/0107789 A1 * | 6/2003 | Hishioka .................... | 359/223 |
| 2006/0140454 A1 * | 6/2006 | Northcott et al. .......... | 382/117 |

OTHER PUBLICATIONS

"Mirao™ 52-e Electromagnetic Deformable Mirror," Imagine Eyes, 2010, 2 pages, [online] [retrieved on Jul. 19, 2010] retrieved from the internet <URL:http://www.imagine-eyes.com/content/view/45/103/>.

"Mirao™ 52-e Electromagnetic Deformable Mirror," Imagine Optic, 2008-2009, 1 page, [online] [retrieved on Jul. 19, 2010] retrieved from the internet <URL:http://www.imagine-optic.com/iop_products_adaptive-optics_mirao-electromagnetic-deformable-mirror_en.php>.

* cited by examiner

*Primary Examiner* — Ricky Mack
*Assistant Examiner* — Mahidere Sahle
(74) *Attorney, Agent, or Firm* — Fenwick & West LLP

(57) ABSTRACT

A rapid iris acquisition, tracking, and imaging system can be used at longer standoff distances and over larger capture volumes, without the active cooperation of subjects. Eye reflections from the subjects' eyes are used to steer a high resolution camera to the eyes in order to capture images of the irises. A circular deformable minor driven by one or more annular forces can be used to focus the camera. A circular mirror substrate is mounted by its circumference onto a minor mount and driven by an annular drive element that contacts the minor substrate along a ring. If the annular drive element has a certain diameter relative to the circumference of the mirror substrate, the mirror substrate will be deformed in the shape of a sphere.

21 Claims, 6 Drawing Sheets

IRIS IMAGING SYSTEM USING CIRCULAR DEFORMABLE MIRROR MOUNTED BY ITS CIRCUMFERENCE

CROSS-REFERENCE TO RELATED APPLICATION(S)

This application claims priority under 35 U.S.C. §119(e) to U.S. Provisional Patent Application Ser. No. 61/076,644, "Circular Deformable Minor Mounted by its Circumference and Driven by an Annular Force," filed Jun. 29, 2008 by Malcolm J. Northcott, et al. The subject matter of the foregoing is incorporated herein by reference in its entirety.

BACKGROUND OF THE INVENTION

1. Field of the Invention

This invention relates to iris imaging systems and to deformable minors, for example as may be used in adaptive optics systems.

2. Background

Biometric identification via iris imaging relies on capturing images of a person's iris and then matching the captured image against a database of previously acquired iris information. In order for this approach to be effective, the subject's iris image must be captured with a certain amount of resolution. Low resolution images do not provide enough information to uniquely match against the database. Furthermore, in many applications, it is desirable to capture iris images from many subjects quickly, non-invasively, and from a distance.

However, many iris imaging systems require correction of optical aberrations (including, for example, focus correction) that would otherwise negatively affect the accuracy, reliability and/or efficiency of the system. To address the problem of optical aberrations in various applications (including iris imaging), adaptive optics systems have been developed to compensate for aberrations. Adaptive optics have been suggested for use in free-space optical communications (e.g., to compensate for atmospheric aberrations and/or to provide fast tracking and focus), astronomy (e.g., to compensate for atmospheric aberrations suffered by land-based telescopes) and, more recently, for iris imaging systems (e.g., to provide fast tracking and auto-focus control).

Some adaptive optics systems use a deformable mirror as the "adaptive" element. However, different types of adaptive optics systems may require differing functionalities and/or optimizations of a deformable mirror. Thus, a deformable mirror that is optimized for one application may not be suitable for a second different application. Conventional designs for deformable mirrors have a number of deficiencies.

One type of deformable minor used is a stack actuator mirror. A stack actuator minor includes a number of push rods that engage the back of a flexible minor so that the extension and retraction of each push rod causes an associated deformation in the minor. However, this type of deformable minor can be expensive, large and relatively slow, since it requires the construction, assembly and alignment of a number of individual push rods. In addition, these deformable mirrors can also exhibit a waffle pattern on the mirror surface, and even higher order modes due to print through. When a small number of actuators are used regular geometry of such a mirror may provide a poor match to the required correction modes for the optical system. Moreover, the number of push rods, the closeness of the push rods, and the length of their travel are physically limited. Since all actuators have the same travel and are attached to a rigid reference surface, the minor has the same stroke for all modes (i.e., low order focus has the same stroke as the highest mode produced by every other actuator being turned on and off.) For correcting the aberrations originating in the atmosphere or many other aberration sources, this range of stroke at the highest modes is not necessary, but the stroke may be inadequate for low order modes. Accordingly, the accuracy and degree of optical correction that can be applied by the stack actuator type minor is also limited in many situations.

Another type of deformable mirror that is becoming commonly used is based on micro-machined-structures (MEMS) fabrication techniques. These mirrors typically have a large number of actuators, but the stroke of the deformable mirror is limited, and they often exhibit high angle scatter due to small scale manufacturing defects. The promise of MEMS technology is low unit price due to economies of scale, but the technology has not yet advanced to the point where low price can be achieved.

Thus, there is a need for improved deformable minors, for use in adaptive optics and other systems.

SUMMARY OF THE INVENTION

The present invention overcomes the limitations of the prior art by providing a circular deformable minor substrate that is mounted by its circumference and is driven by one or more annular forces. In one design, the circumferential minor mount substantially prevents translation of the minor substrate (i.e., no up/down or side/side motion) but allows the minor substrate to tilt locally relative to the minor mount. A single annular force is applied, for example by an annular drive element that contacts the minor substrate but also allows the minor to tilt or otherwise deform locally relative to the drive element. If the annular drive element has the right diameter, then the mirror will always be deformed in the shape of a sphere.

In one embodiment, a deformable mirror is driven by a voice coil. The voice coil may be actuated by any means known to those of skill in the art, including any means for generating a steady force, such as magnetic, electro-magnetic, electrostatic, pneumatic, hydraulic, or mechanical (e.g., lead screw, spring, etc.), for example. The device includes a reflective mirror substrate (i.e., the deformable mirror surface), an inner ring, an outer ring, a permanent magnet, a voice coil, and a housing. The minor substrate is reflective on at least one side, which shall be referred to as the mirror side. The back side of the mirror substrate is mechanically fastened to both the inner and outer rings. The outer ring serves as the mirror mount. It prevents the minor substrate from moving up/down (i.e., in the direction perpendicular to the surface of the mirror) but allows the minor edges to tilt relative to the mirror mount. Thus, in one embodiment, the minor can deform in shape to generate edge tilts in a radial direction. The edge tilts sum to zero around the complete minor circumference.

The inner ring (e.g., an o-ring, or knife edge) is fastened on one side to the back of the minor substrate and is fastened on the other side to a metallic plate. The metallic plate is attached to the permanent magnet. A voice coil (solenoid coil) is positioned at some offset from the back side of the mirror substrate. When electrical current is applied to the voice coil, it induces a magnetic field. This attracts or repels the permanent magnet by some amount of force. The displacement of the permanent magnet exerts force on the inner ring via the metallic plate, thus causing the minor substrate to deform. The diameters of the inner ring and outer ring (and the material properties of the minor substrate) preferably are selected such that force applied to the inner ring will always deform the reflective surface of the minor substrate in the shape of a sphere. In this way, spheres or paraboloids of varying degrees of optical power can be realized. In addition to other practical advantages, the resulting deformable minor has a very high optical quality with minimal high frequency print-through. Also, the deformable minor has a large operational temperature range and exhibits minimal hysteresis.

Other aspects of the invention include adaptive optics systems that use such a deformable mirror, applications for these deformable minors and adaptive optics systems (e.g., in iris imaging systems), and methods corresponding to all of the foregoing.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

As mentioned above, iris imaging is one potential application for adaptive optics and these types of deformable minors. Biometric identification via iris imaging relies on capturing images of a person's iris and then matching the captured image against a database of previously acquired iris information. In order for this approach to be effective, the subject's iris image must be captured with a certain amount of resolution. Furthermore, in many applications, it is desirable to capture iris images from many subjects quickly, with minimal cooperation, and from a distance. For example, it may be desirable to capture iris images of every person passing through an entrance. Thus, an iris imaging system may continuously scan a certain volume in the entrance (the capture volume), capturing iris images of the people in that volume.

Figure 1:
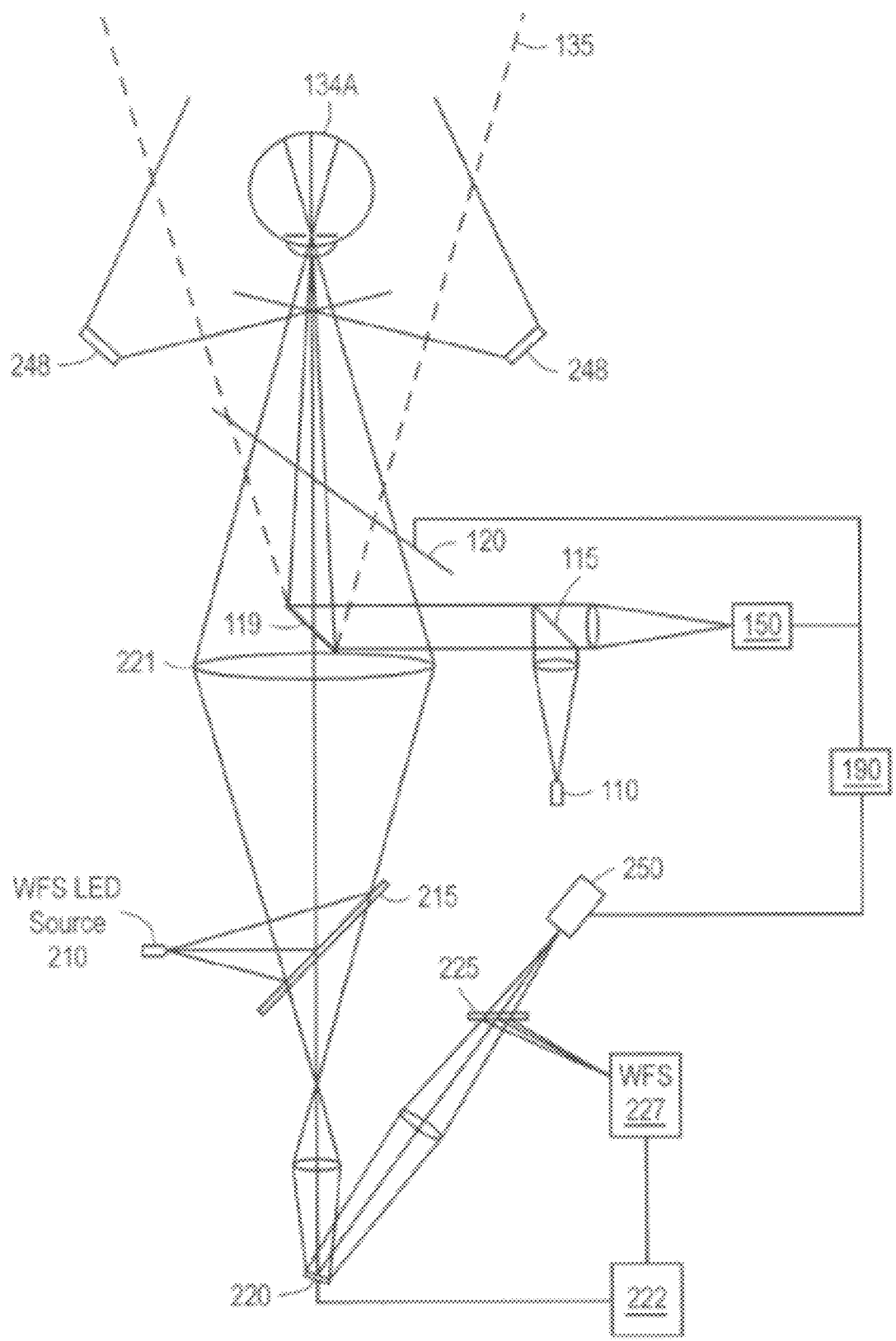
FIG. 1 is an illustration of an iris imaging system that uses an adaptive optics system according to the invention.

FIG. 1 is an illustration of an iris imaging system that uses an adaptive optics system and deformable minor according to the invention. This system is based on retro-reflection from the eye and is designed to capture iris images of many eyes 134 over a large capture volume, typically without the active cooperation of the subjects. In this example, an acquisition subsystem includes a light source 110, a beam splitter 115, a small "pickoff" minor 119 and a camera 150. The acquisition subsystem has a wide field of view and is used to identify the approximate location of each subject.

An imaging subsystem includes a light source 210, a beamsplitter 215, a voice coil deformable mirror 220, a beamsplitter 225, a wavefront sensor 227 and a controller 222. It also includes a light source 248 and a camera 250. The imaging subsystem captures the iris images for each subject. However, in order to obtain sufficient resolution in the iris image, the imaging subsystem has a limited field of view. Therefore, in order to cover the entire capture volume, the imaging subsystem is actively steered from one subject to the next based on information from the acquisition subsystem.

For convenience, the various light sources may be referred to as the acquisition light source 110, the WFS light source 210 and the iris imaging light source 248, respectively, to distinguish them from each other. The iris imaging system also includes a coarse tip-tilt steering minor 120 controlled by controller 190, which is used as part of both the acquisition subsystem 100 and the imaging subsystem 200. Various lenses (or other optics) are used to collimate, focus, image or otherwise relay the optical beams throughout the system.

The acquisition subsystem operates as follows. The acquisition light source 110 is the illumination for camera 150. Light produced by light source 110 reflects off beamsplitter 115, and mirror 119. Beamsplitter 115 separates light produced by source 110 that is exiting the system and light returning to the system to be imaged onto camera 150. Minor 119 combines the optical paths of the acquisition subsystem and the imaging subsystem so they are generally aligned along a common optical axis. In this example, the two subsystems operate at different wavelengths, so minor 119 is a dichroic beamsplitter that reflects the wavelengths of the acquisition subsystem and passes the wavelengths of the imaging subsystem. The outgoing illumination from light source 110 then reflects off coarse steering mirror 120 to illuminate the acquisition subsystem's wider field of view 135. The field of view 135 may stare across the entire capture volume or may be scanned across the capture volume. In this example, the field of view 135 is not wide enough to cover the entire capture volume in a staring mode. Rather, it is scanned across the capture volume by steering minor 120. Subjects within the field of view 135 are represented by eyes 134, which are illuminated by the acquisition light source 110.

Eyes 134 within the field of view 135 retro-reflect light back to the coarse steering minor 120, which directs the light to camera 150 via minor 119 and beamsplitter 115. Camera 150 is a wide angle camera used to identify the general locations of eyes 134. In one implementation, the camera 150 is an electronic image sensor such as a CCD that periodically records discrete images of field of view 135. In one approach, the camera 150 records rapid sequences of images to monitor the movement of objects 134 within the field of view 135. The signals from the wide angle camera are analyzed by software (e.g., contained in controller 190) to identify eyes, which appear as bright circular spots due to the retro-reflections from the eyes 134. The camera 150 operates at the same wavelength as the illuminating source 110. Wavelength filters can be used to reject ambient light on the return optical path, while passing the illuminating wavelength. In addition, the light source 110 can be strobed. Synchronization of the camera 150 exposures with the source 110 strobing can also increase the isolation between imaging and guiding (or wavefront sensor) cameras. Such synchronization can also reduce the effects of background light contamination.

Once eyes 134 are identified, the controller 190 determines a plan for imaging the irises. Preferably, iris images of both eyes are captured (although not necessarily simultaneously), in order to increase the accuracy of identification. In FIG. 1, the iris 134A is being imaged. If necessary, the controller 190 directs the coarse steering mirror 120 to bring the eye of interest 134A within the narrower field of view for the imaging subsystem. As drawn in FIG. 1, the coarse steering minor 120 also steers the wide field of view 135 for the acquisition subsystem, although this is not required. One advantage of steering the acquisition subsystem and imaging subsystem together is that a fixed relationship between the wavefront sensor 227 and the acquisition camera 150 is maintained.

The imaging subsystem operates as follows. WFS light source 210 illuminates the eye 134A. Light produced by light source 210 reflects off beamsplitter 215, propagates through lens system 221 and minor 119, and is directed by steering mirror 120 to the eye 134A. Since this light is coming from the imaging subsystem, it has a narrower field of view than the field of view 135 of the acquisition subsystem. A portion of the illuminating light enters the eye 134A, which retro-reflects light back along the same path 120-221. The return light passes through the beamsplitter 215, reflects off deformable mirror 220 and is directed by beamsplitter 225 to the wavefront sensor 227. The wavefront sensor 227, controller 222 and voice coil deformable minor 220 form an adaptive optics loop that is driven based on the retro-reflected light from the eye 134A.

While adaptive optics can be used in many applications to correct for high order aberrations, in this case, the adaptive optics loop is used mainly for fast tracking of the eye 134A (i.e., correction of tip/tilt errors in the wavefront) and also for focus correction. This keeps the iris 134A within the narrow field of view of camera 250 and also focuses the camera (i.e., images the iris 134A onto the image plane regardless of the object distance to the iris). In this example, the light source 210 does not provide the primary illumination for camera 250. Rather, additional light sources 248 (i.e., the iris imaging light sources) provide off-axis illumination of the irises 134 for camera 250. For example, LEDs in the near infrared wavelength range can be used. The protective pigment melanin is more transparent at longer wavelengths. Thus, the details of the iris structure are more easily seen in heavily pigmented eyes by using light sources of these wavelengths. Alternatively, any other light source could be used that conforms to safety limits. The off-axis illumination generally results in higher contrast and fewer artifacts. Off-axis illumination angle also effects positioning of glints which can be deleterious to the identification accuracy. Glints can also be reduced by using polarized illumination with polarizing filters for the iris camera 250. In alternate approaches, illumination for camera 250 can be provided by ambient lighting, visible or infrared flash, or combinations of these.

In one specific design, the acquisition subsystem has a field of view 135 of approximately 12 degrees, resulting in a capture volume 50 measuring approximately 2 m×2 m×2 m at a 10 m range (without scanning). The acquisition light source 110 is a light-emitting diode (LED) having a wavelength in the range of 750 to 980 nm. Shorter wavelengths give better sensor quantum efficiency, but wavelengths longer than approximately 890 nm are required for invisible operation. Longer wavelengths are also possible but require more expensive (not silicon) detectors. LED sources are generally preferred. Laser sources are problematical due to eye safety considerations, but could be used with careful engineering. Gas discharge lamps could also be used under some circumstances. Thermal sources such as tungsten lights and arc lamps could also be used but would be inefficient due to the requirement for wavelength filtering.

In this specific design, the illuminating wavelength used by the acquisition subsystem is different than that used by the imaging subsystem, so minor 119 can be wavelength-selective to separate the light for the acquisition subsystem from that for the imaging subsystem. The acquisition camera 150 is an infrared enhanced monochrome TV camera with a resolution of approximately 720×500 pixels. The camera 150 operates at a 30 Hz frame rate.

With respect to the imaging subsystem, the resolution requirements drive the design of the iris imaging system. Consider a resolution requirement of 75 microns per pixel. Assuming diffraction limited performance, the required aperture diameter d is given by $d=\lambda z/r$, where z is the object distance and r is the required spatial resolution. For example, assuming $\lambda=0.82$ μm, and z=10 m, the required aperture is 11 cm. As another example, a μm spatial resolution can be achieved at a visible wavelength of 0.5 μm at a 10 m standoff distance with a diffraction limited 5 cm aperture. However, infrared wavelengths are generally preferred for iris imaging due to the enhanced contrast observed at longer wavelengths.

The diffraction limited resolution requirement and large aperture also lead to a limited depth of field. If the geometric image spread due to focus depth of field is set to be less than half of the diffraction limit, then the depth of field l is given by $l=r^2/\lambda$. The 0.82 μm example yields a depth of field of approximately 7 mm. The 0.5 μm example yields a depth of field of approximately 2 cm. Depth of fields on the order of a few millimeters or a few centimeters makes focusing on moving objects difficult. Hence, it is advantageous for the adaptive optics loop to implement fast focus correction as well as fast tracking. With the adaptive optics augmented iris imaging system, images can be taken within a few milliseconds of identifying a target. Thus, the use of adaptive optics can increase the speed and accuracy of image capture for applications involving uncooperative targets.

Figure 2:
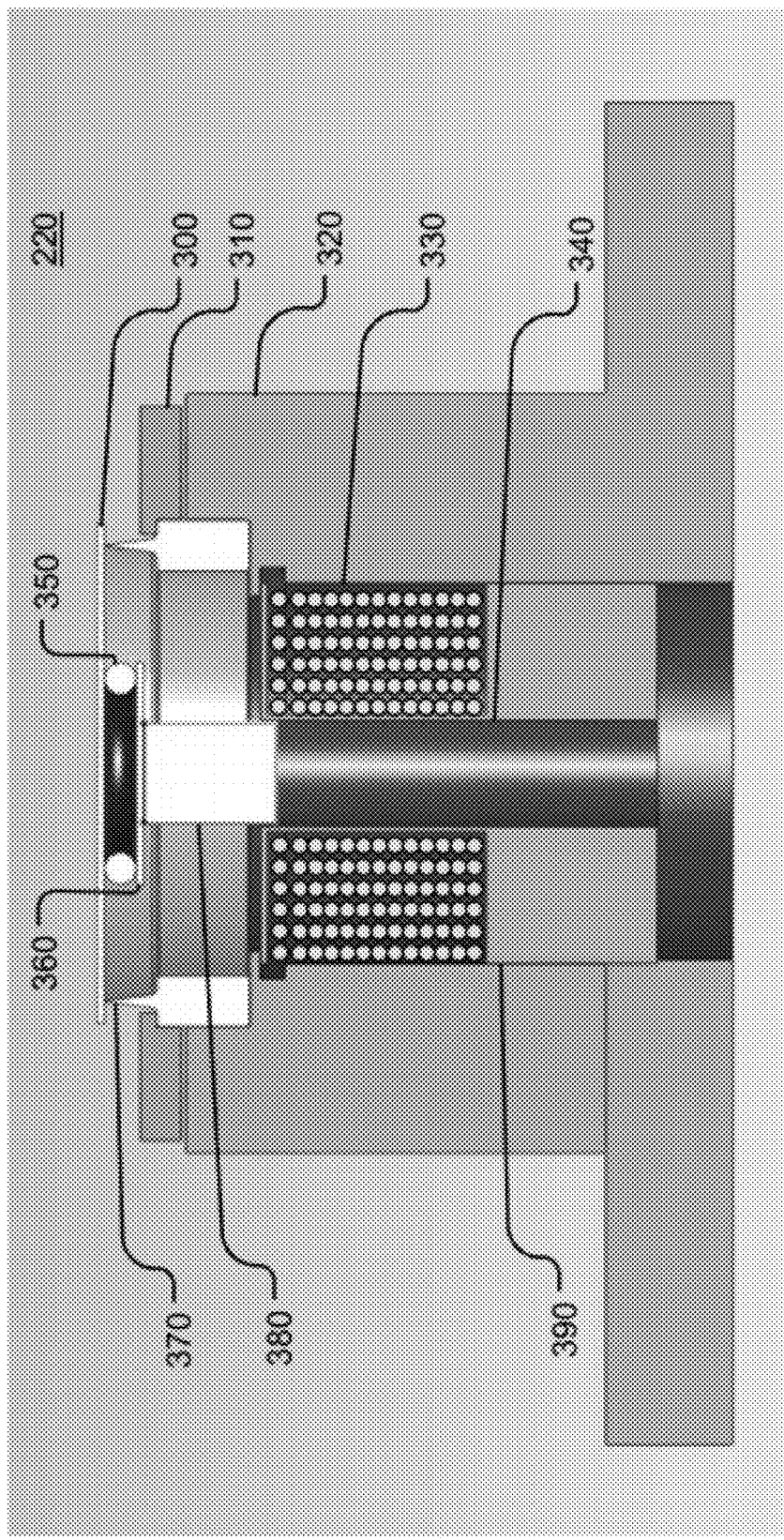
FIG. 2 is a cross-section view of an example deformable mirror according to the invention.

FIG. 2 is a cross-section view of an example deformable mirror 220 according to the invention. This design includes a minor substrate 300, an inner ring 350, an outer ring 370, a permanent magnet 380, and a voice coil or solenoid magnet 330. This particular design also includes a ring clamp 310, a housing 320, and a bobbin 390.

Figure 3A:
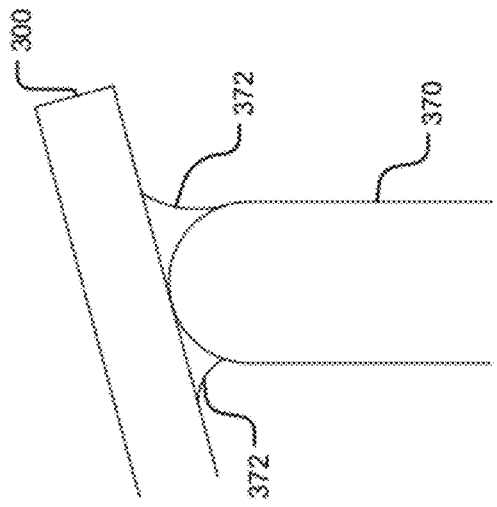
FIGS. 3A and 3B are diagrams illustrating tilting of a reflective mirror substrate relative to its mirror mount.
Figure 3B:
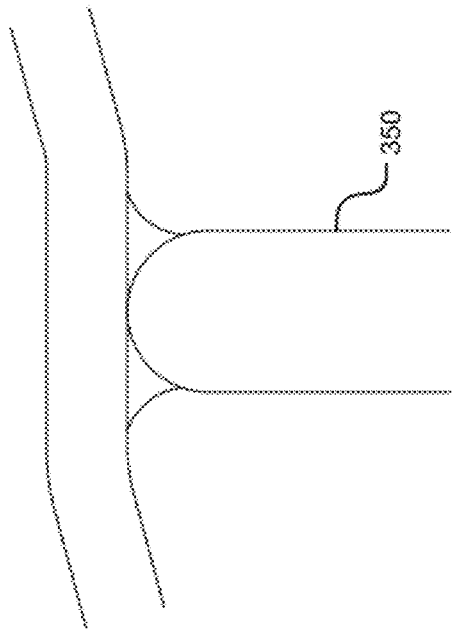

The front surface of mirror substrate 300 is reflective and serves as the optical mirrored surface. The minor substrate 300 is mounted around the circumference of its back side to the front surface of the outer ring 370. The front surface of the outer ring 370 has a rounded edge along which mirror substrate 300 can tilt in a radial direction when a bending force is applied to the mirror. In this particular example, the minor substrate 300 is fastened to the outer ring 370 by a soft RTD glue joint 372, as shown in FIGS. 3A-3B. The glue joint 372 is strong enough to substantially prevent horizontal and vertical translation of the substrate 300. However, it is compliant enough to allow the substrate to tilt along the rounded top edge of the outer ring 370. FIG. 3A shows the minor substrate 300 when no force is applied. FIG. 3B shows the minor substrate 300 tilting along the top edge when a force pulls the mirror substrate 300 towards the voice coil 330. For this application, the glue joint has a high plasticity limit sufficient to allow the joint to withstand many cycles of tilting and/or deformation.

For convenience, the terms circular minor or circular mirror substrate will be used to describe the minor substrate 300 and its reflective surface, and the term circumferential minor mount will be used to describe the outer ring 370. These terms are not meant to imply that the minor substrate 300 must be perfectly circular or that the outer ring 370 must contact the mirror substrate 300 at the exact outer edge of the substrate. As shown in FIGS. 2-3, the outer ring 370 typically will support the minor substrate 300 approximately but not exactly at its circumference. The mirror substrate 300 typically will have some overhang.

In one embodiment, the force is applied through the inner ring 350. One side of the inner ring 350 is attached to the back side of the mirror substrate 300. In this particular example, the inner ring 350 is secured to the mirror substrate 300 in a similar manner as the outer ring 370. That is, a glue joint formed from a soft RTD glue ensures that up/down force is efficiently transferred from the inner ring 350 to the mirror substrate 300. However, the glue joint is compliant enough to allow the substrate to tilt, and has a plasticity limit that enables the joint to withstand many cycles of tilting and deformation. In another embodiment, a glue joint is applied at the inner ring 350, and the outer ring 370 is used to apply the force. In this arrangement, bidirectional operation can be arranged by suitably biasing the shape of the mirror.

Figure 4A:
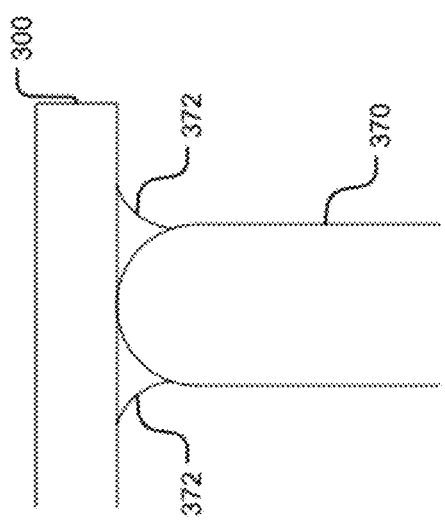
FIG. 4A is a diagram illustrating free tilting of a reflective substrate attached compliantly to a drive element.
Figure 4B:
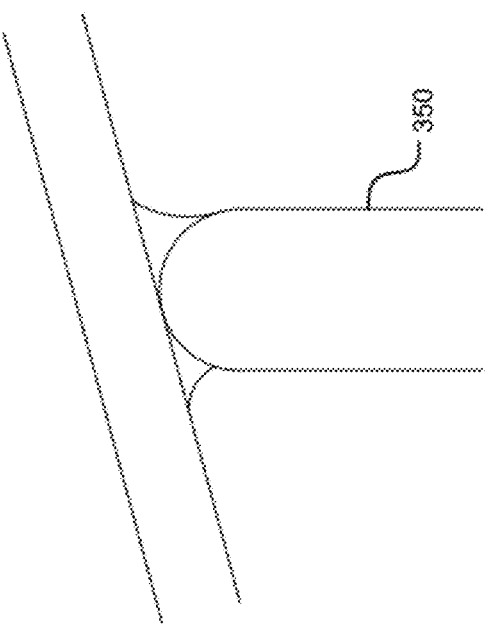
FIG. 4B is a diagram illustrating no tilting of a reflective substrate attached rigidly to a drive element.

In one embodiment, since both the inner ring 350 and outer ring 370 have glue joints that freely allow radial tilting of the mirror substrate, the mirror substrate has the freedom of motion to assume a natural position without unnatural discontinuities at either point of attachment. FIGS. 4A-4B illustrate this. FIG. 4A shows the mirror substrate 300 and inner ring 350 when the glue joint is compliant. FIG. 4B shows the mirror substrate 300 and inner ring 350 when the glue joint is so stiff that it forces the mirror substrate to be level at the point of attachment. This results in a "kink" in the mirror where the mirror would otherwise be tilted, as shown in FIG. 4A.

The other side of the inner ring 350 is attached to the front surface of metallic plate 360. The back surface of metallic plate 360 is attached to a permanent magnet 380. A voice coil 330 is positioned at some offset from the back surface of the mirror substrate 300. Upon the wavefront sensor 227 detecting an aberration in a wavefront, the controller 222 generates an electrical current calculated to correct the wavefront. The electrical current is applied to the voice coil 330, inducing a magnetic field. The magnetic field from the permanent magnet 380 reacts to the magnet field from the voice coil 330, displacing the permanent magnet 380 in cavity 340. The displacement of the permanent magnet 380 pulls (or pushes) the metallic plate 360 and the inner ring 350, causing the mirror substrate 300 to deform.

Optionally, the diameters of inner ring 350 and outer ring 370 can be selected so that the applied force causes the mirror substrate 300 to always deform in the shape of a sphere. The sphere is a preferred shape for optical correction. Spheres of varying radii correspond to varying degrees of optical power.

The solution for the deformation of an axially symmetric thin plate is obtained in close form using cylindrical coordinates:

$$w[r]=(r^4P)/(64D)r^4+AAr^2+BB \log [r]+CC+FFr^2 \log [r] \quad (1)$$

where w is the deflection, r is the radial coordinate P is a uniform pressure (zero in one implementation) and D is the bending stiffness. AA, BB, CC, and FF are arbitrary constants that are calculated from the boundary conditions.

$$D=Eh^3/(12(1-v^2)) \quad (2)$$

where E is the modulus, h the thickness of the plate and v is the Poisson ratio.

For the interior of the inner ring and P=0 (zero pressure), Eq. (1) simplifies to $$w[r]=CC+AAr^2 \quad (3)$$

The constants BB and FF need to be zero to avoid the singularity at in the center of the structure. As can be seen, the solution is a paraboloid which closely approximates a sphere for small deflections.

Returning to FIG. 2, the back surface of outer ring 370 is seated in a groove in housing 320. The outer ring 370 is then held in place by ring clamp 310. The bobbin 390 insulates and protects the wiring of voice coil 330.

This deformable mirror design has many advantages compared to conventional designs. These advantages include lower cost and more repeatable manufacturability. In addition, a simpler controller can be used since the deformable mirror basically has only one degree of freedom—the optical power. In addition, the deformable mirror has a very high optical quality with minimal high frequency print-through. Also, the deformable mirror has a large operational temperature range and exhibits minimal hysteresis.

One particular implementation suitable for use with the iris imaging system described above uses BK7 at a typical thickness of 0.25 mm. The diameter of the BK7 glass substrate is 1 inch, the outer ring approximately 0.9 inch, and the inner ring ⅜ inch. A stroke of +/−1.3 diopters is obtained at a drive current of +/−0.7 ampere. A Nb rare earth magnet of ¼ inch diameter by ⅜ inch long is used. In this implementation, a voice coil with about 500 turns is used.

The deformable mirror shown in FIGS. 2-4 is just one example. Other variations will be apparent. For example, the mirror substrate 300 in this example is a thin sheet of glass that is optically polished and coated on the mirror side. Other designs for substrate 300 could be used. For example, a metal plate, silicon carbide, hard plastics, or ceramics may also be used as the substrate 300.

In addition, the inner and outer rings 350, 370 could be constructed differently, and the mechanical joints between the rings and the mirror substrate 300 could also be made in other ways. For example, the mechanical joints may be flexible hinges made with EDM micromachining or other techniques, or may comprise force contact with force possible bias to maintain a positive force under all required actuation conditions, or apposing ball bearing races. The mirror mount 370 also is not required to contact the mirror substrate 300 on its back surface. It could make contact the front surface (i.e., mirrored surface) instead of or in addition to the back surface.

Figure 5:
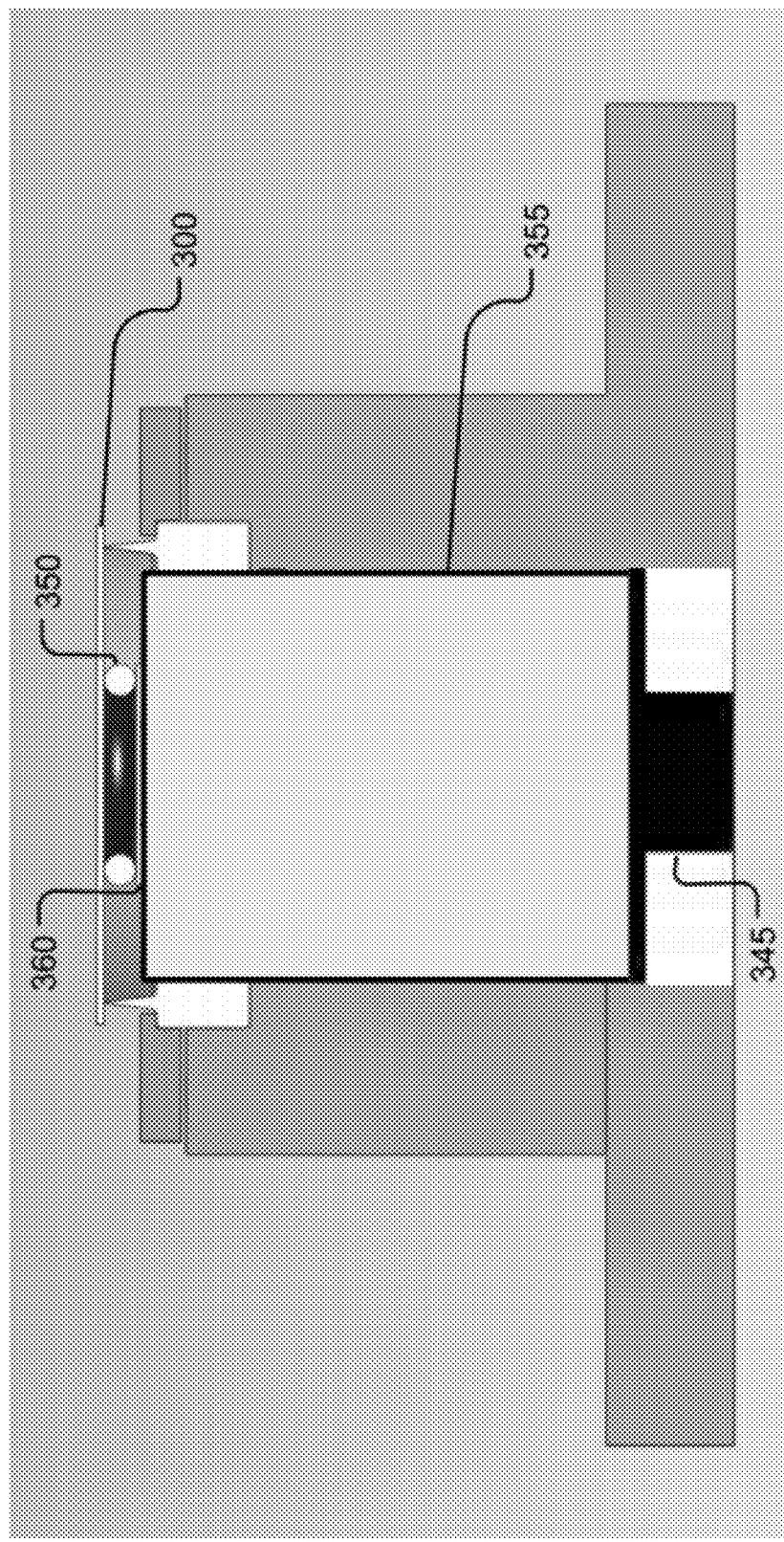
FIG. 5 is a cross-section view of another example deformable minor according to the invention.

As another variation, the annular force can be applied to the mirror substrate using annular drive elements other than the permanent magnet 380/voice coil 330 assembly shown in FIGS. 2-3. For example, FIG. 5 depicts an alternative embodiment in which the permanent magnet/voice coil assembly is replaced by an actuator 345 that drives a volume of fluid 355 (e.g., oil, water, air) within housing 320. Upon the wavefront sensor 227 detecting an aberration in a wavefront, the controller 222 generates an electrical current calculated to correct the wavefront. The electrical current is applied to actuator 345, causing the actuator 345 to be displaced towards or away from the mirror substrate 300. This causes the fluid to exert a force on the metallic plate 360 that pushes the inner ring 350, causing the mirror substrate 300 to deform. Alternatively, as mentioned above, the voice coil may be actuated by any means known to those of skill in the art, including any means for generating a steady force, such as magnetic, electro-magnetic, electrostatic, pneumatic, hydraulic, or mechanical (e.g., lead screw, spring, etc.), for example.

Other designs incorporating voice coils are also possible. Specifically, there are many other arrangements of coils, as well as arrangements with coils with magnets that can be used to generate the required forces on the deformable mirror. For example, in one design, a coil is attached to the deformable mirror and to fixed magnets.

Figure 6A:
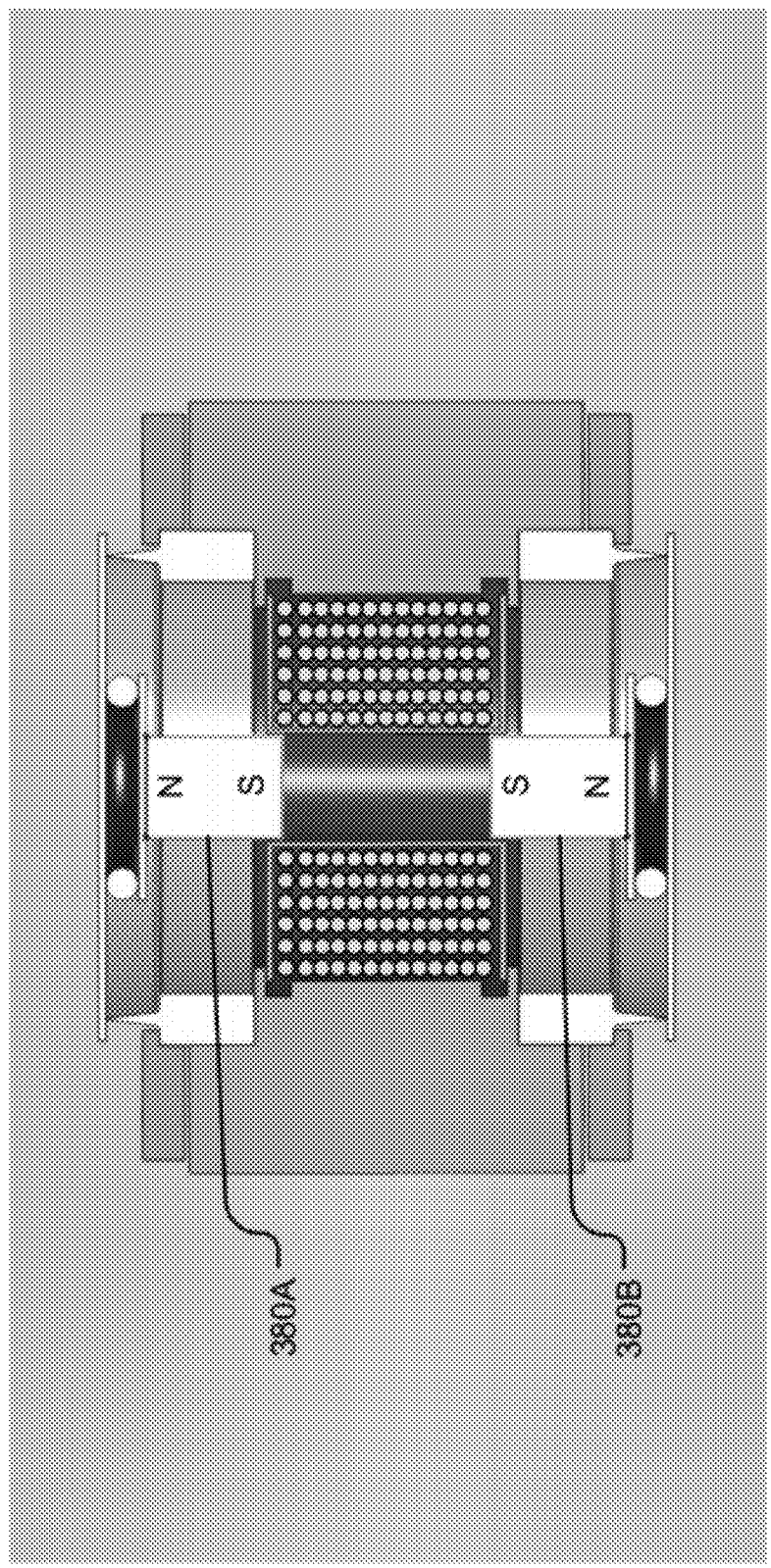
FIGS. 6A and 6B are cross-section views of example deformable minors according to the invention.
Figure 6B:
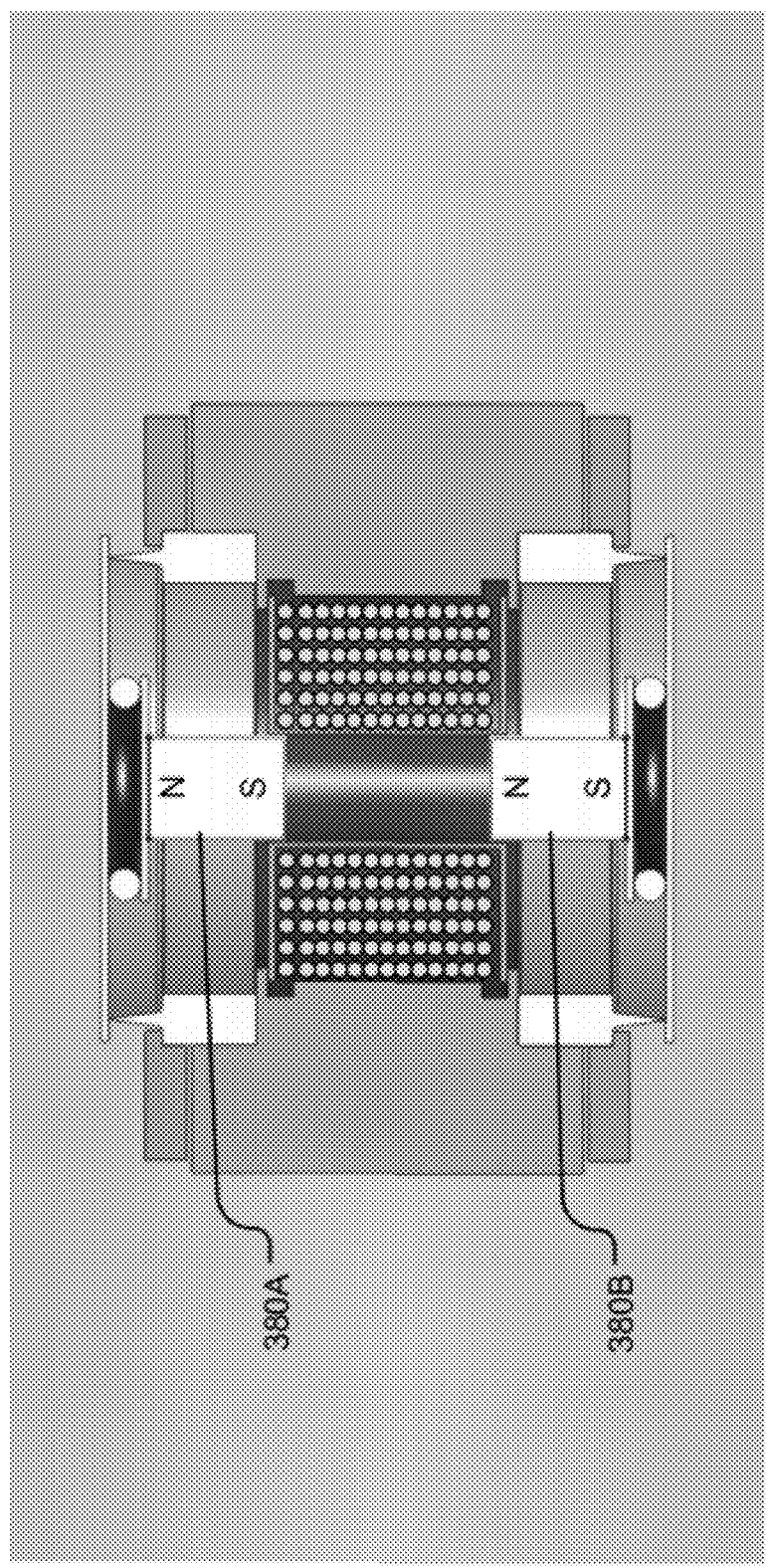

In yet another embodiment, the same voice coil (or other annular drive element) can be used to drive two mirror substrates. FIG. 6A shows an example where the mirror substrates are used in a push-pull configuration due to the polarity of the permanent magnets. That is, one substrate is pushed when the other is pulled. Thus, the two mirror substrates deform to a shape with opposite optical powers. FIG. 6B shows an example where the voice coil exerts the same polarity force on both minor substrates, thus deforming both mirror substrates to a shape with the same optical power.

As a final example, by varying the diameter of the inner ring 350, shapes other than spheres can be realized. By using more than one inner ring 350 (i.e., by applying annular forces at more than one diameter), more complex shapes can also be realized.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. An iris imaging system comprising an imaging subsystem, the imaging subsystem comprising:
    a camera for capturing images of irises with sufficient resolution for biometric identification;
    a light source for producing light to illuminate eyes; and
    a fine tracking system for steering the camera to eyes, based on an eye reflection of the light illuminating the eyes, the fine tracking system including:
        a deformable mirror for both steering the camera to the eyes and adjusting a wavefront of the eye reflected light, the deformable mirror including a circular mirror substrate attached by a flexible joint around which the mirror substrate can tilt to an annular mechanical drive element, the circular mirror substrate mounted on a circumferential mirror mount, the circular mirror substrate having a reflective front surface and a back surface, the circumferential mirror mount substantially preventing translation of the mirror substrate relative to the mirror mount but permitting the mirror substrate to tilt locally relative to the mirror mount, and the annular mechanical drive element applying an annular force to the back surface of the mirror substrate;
        a wavefront sensor for sensing the wavefront of the eye reflected light; and
        a controller coupled between the deformable mirror and the wavefront sensor, for adjusting the deformable mirror based on the sensed wavefront.

2. The iris imaging system of claim 1, wherein the camera captures images of irises with a resolution of 200 microns or better.

3. The iris imaging system of claim 1, wherein the imaging subsystem can cover a capture volume of at least 1 cubic meter.

4. The iris imaging system of claim 1, wherein the camera can capture iris images at a standoff of at least 5 m.

5. A deformable mirror, comprising:
    a circular mirror substrate mounted on a circumferential mirror mount, the circular mirror substrate having a reflective front surface and a back surface, the circumferential mirror mount substantially preventing translation of the mirror substrate relative to the mirror mount but permitting the mirror substrate to tilt locally relative to the mirror mount; and
    an annular mechanical drive element that applies an annular force to the back surface of the mirror substrate, the annular mechanical drive element being attached to the back surface of the mirror substrate by a first flexible joint around which the mirror substrate can tilt when the annular force is applied.

6. The deformable mirror of claim 5, wherein the circumferential mirror mount includes a first ring, the first ring having a rounded top edge fastened to the back surface of the mirror substrate by a second flexible joint around which the mirror substrate can tilt when the annular force is applied to the mirror substrate.

7. The deformable mirror of claim 6, wherein the second flexible joint is an adhesive joint.

8. The deformable mirror of claim 7, wherein the second flexible joint is formed from a soft RTD glue.

9. The deformable mirror of claim 6, further comprising a ring clamp that secures the first ring in place.

10. The deformable mirror of claim 5, wherein the annular mechanical drive element includes a second ring, the second ring having a rounded top edge fastened to the back surface of the mirror substrate by the first flexible joint.

11. The deformable mirror of claim 10, wherein the first flexible joint is an adhesive joint.

12. The deformable mirror of claim 11, wherein the first flexible joint is formed from a soft RTD glue.

13. The deformable mirror of claim 5, wherein:
    the circumferential mirror mount includes a first ring, the first ring having a rounded top edge fastened to the back surface of the mirror substrate by a second flexible joint around which the mirror substrate can tilt in a radial direction when the annular force is applied to the mirror substrate; and
    the annular drive element includes a second ring, the second ring having a rounded top edge fastened to the back surface of the mirror substrate by the first flexible joint.

14. The deformable mirror of claim 13, wherein the diameters of the first ring and the second ring are selected such that the reflective front surface deforms in a spherical shape when the annular force is applied to the mirror substrate.

15. The deformable mirror of claim 5, wherein the annular drive element includes:
    a permanent magnet fastened to the back surface of the mirror substrate; and
    a voice coil positioned at an offset from the back surface of the mirror substrate.

16. The deformable mirror of claim 15, wherein the voice coil is positioned at an angle relative to the mirror mount.

17. The deformable mirror of claim 5, wherein the annular drive element includes:
    a variable shape fluid-tight housing filled with a pressurized fluid, the housing transmitting the annular force to the back surface of the mirror substrate when the housing changes shape; and
    an actuator that changes a volume of the housing, thereby causing the housing to change shape.

18. The deformable mirror of claim 5, further comprising:
    a second circular mirror substrate mounted on a second circumferential mirror mount, the second circular mirror substrate having a reflective front surface and a back surface, the second circumferential mirror mount substantially preventing translation of the second mirror substrate relative to the second mirror mount but permitting the second mirror substrate to tilt locally relative to the second mirror mount, the annular mechanical drive element also applying a second annular force to the back surface of the second mirror substrate.

19. The deformable mirror of claim 18, wherein the two mirror substrates deform to a shape with a same optical power.

20. The deformable mirror of claim 18, wherein the two mirror substrates deform to a shape with opposite optical powers.

21. A deformable mirror comprising:
- a circular mirror substrate having a reflective front surface and a back surface;
- a circumferential mirror mount comprising an outer ring with a rounded top edge and a first soft RTD glue joint fastening the back surface of the mirror substrate to the rounded top edge of the outer ring, the first RTD glue joint substantially preventing translation of the mirror substrate relative to the outer ring but permitting the mirror substrate to tilt around the rounded top edge of the outer ring;
- an inner ring with a rounded top edge and a second soft RTD glue joint fastening the back surface of the mirror substrate to the rounded top edge of the inner ring, the second RTD glue joint substantially preventing translation of the mirror substrate relative to the inner ring but permitting the mirror substrate to tilt around the rounded top edge of the inner ring;
- a permanent magnet fastened to a back side of the inner ring; and
- voice coil positioned at an offset from the back surface of the mirror substrate.

* * * * *